United States Patent
Thompson

(10) Patent No.: US 6,689,162 B1
(45) Date of Patent: Feb. 10, 2004

(54) BRAIDED COMPOSITE PROSTHESIS

(75) Inventor: Paul J. Thompson, New Hope, MN (US)

(73) Assignee: Boston Scientific SciMed, Inc., Natick, MA (US)

( * ) Notice: Subject to any disclaimer, the term of this patent is extended or adjusted under 35 U.S.C. 154(b) by 0 days.

(21) Appl. No.: 09/496,088

(22) Filed: Feb. 1, 2000

Related U.S. Application Data

(62) Division of application No. 08/919,428, filed on Aug. 27, 1997, now Pat. No. 6,019,786, which is a division of application No. 08/640,062, filed on Apr. 30, 1996, now Pat. No. 5,758,562.
(60) Provisional application No. 60/005,209, filed on Oct. 11, 1995.

(51) Int. Cl.$^7$ .................................................. A61F 2/06
(52) U.S. Cl. ..................................... 623/1.53; 623/1.18
(58) Field of Search ................ 606/191, 198; 623/1.11, 1.15, 1.18, 1.53

(56) References Cited

U.S. PATENT DOCUMENTS

| | | | | |
|---|---|---|---|---|
| 4,655,771 A | * | 4/1987 | Wallsten ......................... 623/1 |
| 4,834,755 A | * | 5/1989 | Silvestrini et al. ............. 623/13 |
| 5,197,978 A | * | 3/1993 | Hess ............................. 623/1 |
| 5,423,849 A | * | 6/1995 | Engelson et al. ........... 606/191 |
| 5,476,507 A | * | 12/1995 | Wakabayashi et al. ...... 623/1.54 |
| 5,562,725 A | * | 10/1996 | Schmitt et al. ............. 623/1.53 |
| 5,697,969 A | * | 12/1997 | Schmitt et al. ............. 623/1.44 |
| 5,891,193 A | * | 4/1999 | Robinson et al. ............ 128/898 |
| 6,019,786 A | * | 2/2000 | Thompson ..................... 623/1 |
| 6,221,099 B1 | * | 4/2001 | Andersen et al. ........... 623/1.15 |
| 6,342,068 B1 | * | 1/2002 | Thompson .................. 623/1.53 |
| 2001/0000188 | * | 4/2001 | Lenker et al. .............. 623/1.13 |
| 2001/0056299 | * | 12/2001 | Thompson .................. 623/1.53 |

\* cited by examiner

*Primary Examiner*—Paul B. Prebilic
(74) *Attorney, Agent, or Firm*—Larkin Hoffman Daly & Lindgren, Ltd.; Frederick W. Niebuhr, Esq.

(57) ABSTRACT

A prothesis for transluminal implantation consists of a flexible tubular interbraided structure of metal or polymeric monofilaments, and polymeric multifilament yarns. The prosthesis can be elastically deformed to reduce its diameter through axial elongation. The monofilaments and multifilament yarns are arranged in axially spaced apart helices, concentric on a common central axis of the prosthesis. The monofilaments are selectively shaped before their interbraiding with the multifilament yarns, either by an age-hardening or other heat-setting stage, or a cold-working stage that controllably plastically deforms the strands. The shaped structural strands cooperate to impart to the prosthesis its nominal shape and resilience. The textile strands cooperate to provide a sheeting that occupies interstices between adjacent structural strands, to reduce permeability and thereby enhance the utility of the prosthesis as a vascular graft. An alternative embodiment prosthesis includes elastically and plastically deformable structural strands, selectively plastically deformed by cold-working then interbraided to form the prosthesis.

22 Claims, 9 Drawing Sheets

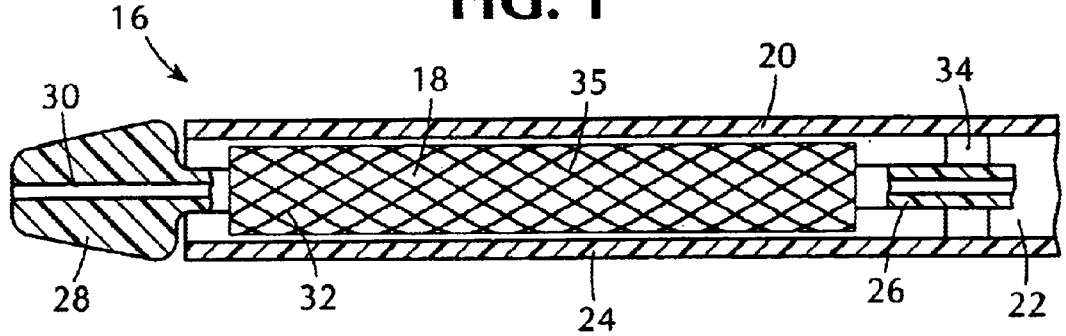
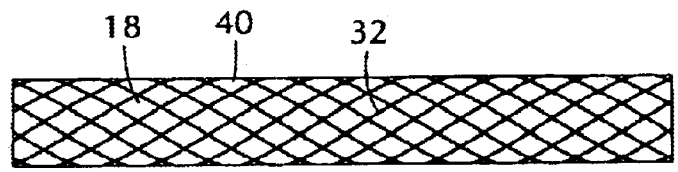
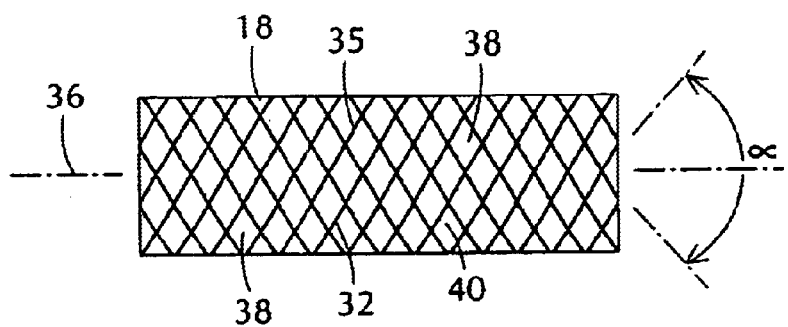

BRAIDED COMPOSITE PROSTHESIS

This is a divisional of prior application Ser. No. 08/919,428 (now U.S. Pat. No. 6,019,786), filed Aug. 27, 1997 as a divisional of application Ser. No. 08/640,062 (now U.S. Pat. No. 5,758,562), filed Apr. 30, 1996 and claiming the benefit of Provisional Patent Application No. 60/005,209 filed Oct. 11, 1995.

BACKGROUND OF THE INVENTION

The present invention relates to body implantable devices, and more particularly to prostheses including stents and grafts intended for long term or permanent intraluminal fixation.

A variety of patient treatment and diagnostic procedures involve the use of devices inserted into the body of a patient and intraluminally implanted. Among these devices are prostheses as disclosed in U.S. Pat. No. 4,655,771 (Wallsten). These devices are flexible, tubular, braided structures formed of helically wound thread elements. A delivery catheter includes gripping members for securing a prosthesis to the catheter. In deployment, the gripping members and catheter are removed, allowing the prosthesis to assume a substantially cylindrical shape as it radially expands and substantially conforms to a blood vessel wall or other tissue.

Metallic thread elements or strands are generally favored for applications requiring flexibility and effective resistance to radial compression after implantation. Metallic strands can be thermally formed by a moderately high temperature age-hardening process while wound about a mandrel in the desired helical configuration. The strands cooperate to provide the requisite strength, due to their high modulus of elasticity.

The flexibility of the strands also is important, as it permits a radial compression of the stent (by an axial elongation) that facilitates delivery of the stent through narrow blood vessels or other lumens toward the intended treatment site. Because the self-expanding device generally remains at least slightly radially compressed after fixation, its restoring force can provide acute fixation. The flexible stent can accommodate a wider range of lumen diameters, reducing the need to precisely match the'stent and lumen as to size. The favorable combination of strength and flexibility is due to the properties of the strands themselves, and the arrangement of strands, i.e. the axial spacing between adjacent helical strands, the braiding angles of the strands, etc. Accordingly, stents characteristically have an open mesh construction as shown in FIGS. 2a and 2b.

U.S. Pat. No. 4,681,110 (Wiktor) discloses a flexible tubular liner, insertable into the aorta to treat an aneurisym. The liner is a tight weave of flexible plastic strands, designed to self-expand against the aneurisym to direct blood flow past the aneurisym. In this context, a tight weave is intended to minimize leakage, so that the liner can effectively shunt blood through to eliminate the aneurysmal sack from the blood path.

Those of skill in the art have generally encountered difficulty in providing a device that simultaneously accommodates the competing needs of low permeability, and strength and flexibility for considerable radial compression and expansion.

One known approach to counter this problem is a combination stent/graft, in which a compliant but substantially fixed-radius and tightly-woven graft is sutured or otherwise coupled to a radially expandable stent. The stent upon release is intended to radially expand to the graft diameter. This, however, generally requires a careful matching of the graft diameter with the lumen diameter at the treatment site. Otherwise, either an oversized graft is compressed between the stent and body tissue with undesirable folds or gathering of the graft material, or an undersized graft prevents the stent from expanding sufficiently to anchor the device.

Several prosthesis constructions have been suggested, particularly involving three dimensional braiding as disclosed in International Patent Publications No. WO91/10766. For example, see International Patent Publication No. WO92/16166, No. WO94/06372, and No. WO94/06373. These publications discuss composite grafts or other braided structures that combine different types of strands, e.g. multifilament yarns, monofilaments, fusible materials, and collagens. In all of these disclosures, the woven or braided structure is heat set after braiding to impart the desired nominal shape to the device. Accordingly, all strands and filaments must be compatible with the heat set conditions (primarily the high temperature), limiting the type of materials that can be interbraided into the device.

Therefore, it is an object of the present invention to provide a prosthesis including structural strands and other strands interbraided with the structural strands, in which the types of materials for such other strands are not limited by conditions necessary to thermally set or otherwise selectively shape the structural strands.

Another object is to provide a process for making a prosthesis, in which a certain portion of the strands ultimately incorporated into the prosthesis, e.g. structural strands, can be treated to assume predetermined nominal shapes without any undesirable impact on the other strands incorporated into the structure.

A further object is to provide, in a prosthesis manufacturing process involving the interbraiding of multiple strands, a means for selectively cold-working a portion of the strands to predetermine a nominal shape of the interbraided structure.

Yet another object is to provide an interbraided device incorporating the strength, resilience and range of diameters associated with stents, and the low permeability associated with grafts.

SUMMARY OF THE INVENTION

To achieve these and other objects, there is provided a process for making a prosthesis, including the following steps:

a. providing a plurality of structural strands formed of structural material and having an original nominal shape, and providing a plurality of compliant textile strands;

b. altering the structural strands to impart to each of the structural strands a selected nominal shape in lieu of the original nominal shape; and c. after altering, braiding the strands into an integrated structure of the structural strands and the textile strands.

Preferably the braiding forms a latticework of the structural strands. Then, the textile strands are formed as a textile sheeting that is supported by the latticework and occupies interstices between adjacent structural strands of the latticework.

A salient feature of the process is that the structural strands are selectively shaped, i.e. given their predetermined second nominal shapes, prior to the interbraiding step. Consequently, process conditions for selective shaping have virtually no impact on the textile strands. This is particularly beneficial when the structural strands are metallic, e.g. formed of Elgiloy or another cobalt-based alloy, certain stainless steels, or a recovery metal such as Nitinol nickel-titanium alloy. These metals provide the desired strength and resiliency, yet when thermally shaped require temperatures far above the melting points typical of the multifilament yarns suitable for the textile strands. In certain cases, significant damage can occur below (although near) the melting point. Certain polymers suitable for the structural strands likewise are advantageously shaped at temperatures unsuitably high for the textile strands. In either event, thermally setting or shaping the structural strands prior to interbraiding prevents this kind of damage to the textile strands.

In accordance with the present invention, structural strands may be selectively shaped by cold working as well. Certain resilient and ductile metals are particularly well suited to cold working. A primary advantage is the ability to incorporate the cold-working step and the braiding step into a continuous operation. In particular, each structural strand on its way to a braiding station can be wrapped about a shaping pulley under sufficient tension to achieve the needed plastic deformation. Continuous shaping and braiding can substantially reduce manufacturing cost.

The structural strands can be formed into a variety of shapes, most preferably helical. The helices can be wound in a single direction so that the interstices are helical. More frequently, the structural strands are wound as two sets of helices running in opposite directions, to form a latticework in which the interstices are rhombic. The oppositely directed helices can be interbraided, or can overlie one another, being interbraided only with the textile strands. The interbraided structure can incorporate further strands, for example of radiopaque material. The structure can incorporate one or more elastomeric strands running axially of the structure and fused to the structure along at least part of its axial length, thus to enhance radial self-expansion.

The process can be augmented with several steps that enhance the utility of the prosthesis, such as coating the structural strands, the textile strands, or both. A heat setting step may be performed after braiding, when the textile strands are formed of a yarn amenable to heat setting. An adhesive can be applied to the ends of the integrated structure after braiding, to reduce or prevent unraveling.

Another aspect of the present invention is a prosthesis. The prosthesis includes an integrated structure including an interbraiding of a plurality of structural strands and a plurality of compliant textile strands. The structural strands are formed of a structural material having a tendency to assume a nominal shape when in a relaxed state. The structural strands further have respective selected nominal strand shapes imparted by at least one of: (i) a selective plastic deformation from an original nominal strand shape to the selected nominal strand shape; and (ii) a selective thermal setting including a heating of the structural strand to a temperature greater than a melting temperature of the textile strands while the structural strand is maintained in the selected nominal strand shape.

The structural strands have selected orientations within the integrated structure, to impart a predetermined nominal shape to the integrated structure. In a preferred prosthesis, the structural strands cooperate to form a latticework, and the textile strands cooperate to form a textile sheeting supported by the latticework and occupying interstices between adjacent structural strands of the latticework. Thus, the structural strength and resiliency of a self-expanding stent and the low permeability of a graft are combined in a single prosthesis.

The structural strands preferably are monofilaments of metal, e.g. a stainless steel, an alloy including cobalt or an alloy including titanium. Alternatively the monofilaments are polymeric, constructed of materials including PET, polypropylene, PEEK, HDPE, polysulfone, acetyl, PTFE, FEP, polycarbonate urethane, and polyurethane. In either event the preferred textile strands are multifilament polymeric yarns. Suitable materials for the multifilament yarns include PET, polypropylene, polyurethane, polycarbonate urethane, HDPE (high density polyethylene), polyethylene, silicone, PTFE, ePTFE and polyolefin.

Thus in accordance with the present invention, an interbraided structure incorporating structural and textile strands is manufactured according to a process that enables a controlled shaping of the structural strands without adversely affecting the textile strands. The result is an intraluminal device with the favorable qualities of an open weave stent and of a tightly woven graft. The structural strands are shaped either thermally or by plastic deformation, before they are brought together with the textile strands for interbraiding. The interbraiding step involves all strands simultaneously, interweaving a compliant textile sheeting among the structural strands as the structural strands are formed into a latticework that defines the shape of the prosthesis. As a result, the textile sheeting is supported by the latticework and tends to conform to the shape of the latticework. The textile sheeting exhibits low permeability and high compliance, occupying and more preferably filling the voids between adjacent structural strands to prevent leakage of blood or other fluids, yet readily conforming to the shapes of the voids, as these shapes change responsive to radial contractions and expansions of the structure.

IN THE DRAWINGS

For a further understanding of the above and other features and advantages/reference is made to the following detailed description and to the drawings, in which:

FIG. 1 is a partial side sectional view of a prosthesis constructed in accordance with the present invention, contained within a deployment device;

FIGS. 3 and 4 show the prosthesis of FIG. 1 in a radially constrained state, and in a radially expanded state, respectively;

Figure 7:
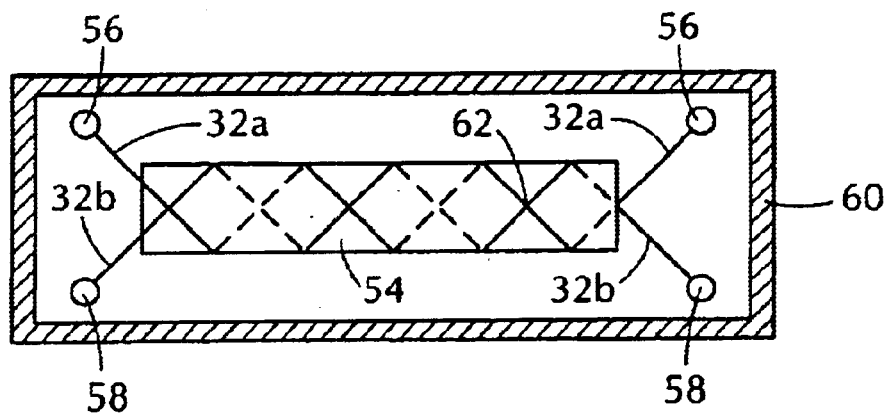
Figure 8:
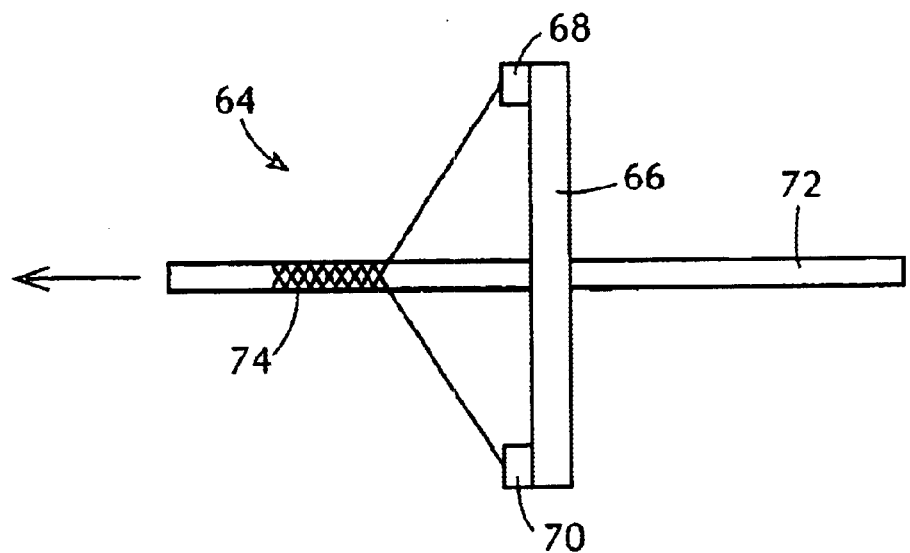
Figure 9:
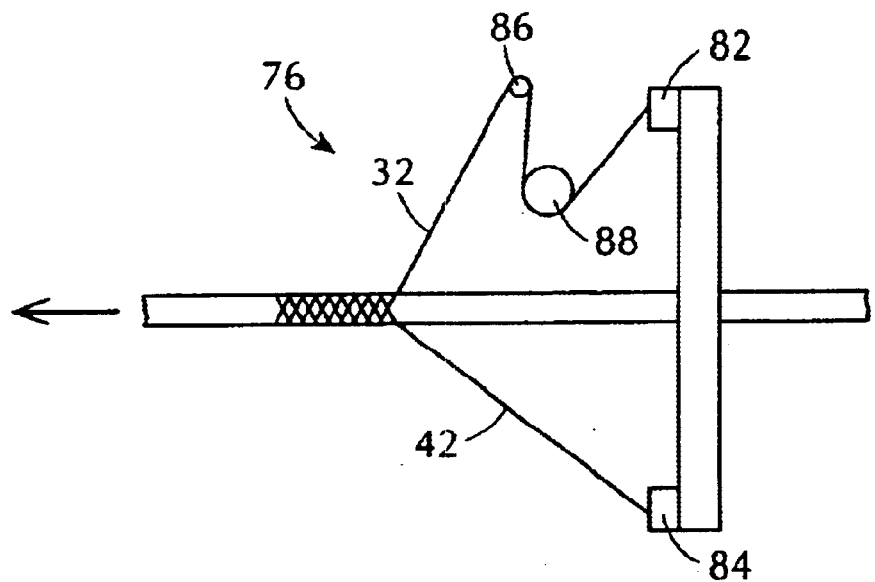
Figure 10:
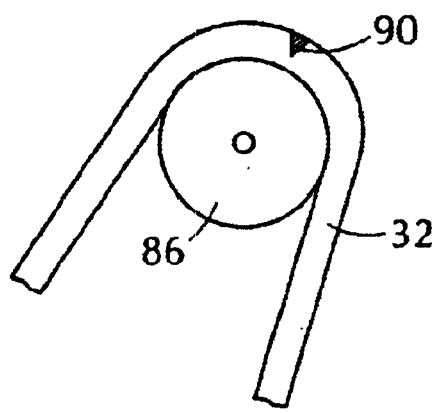
Figure 11A:
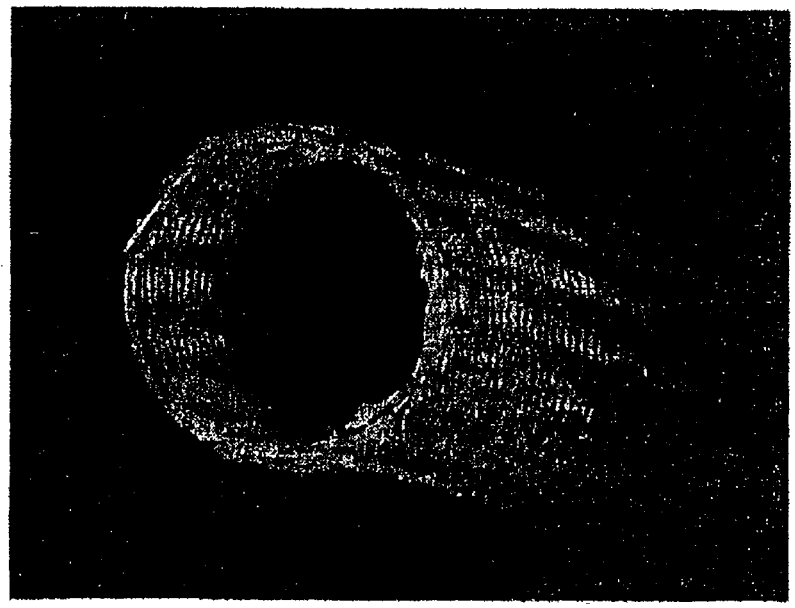
Figure 11B:
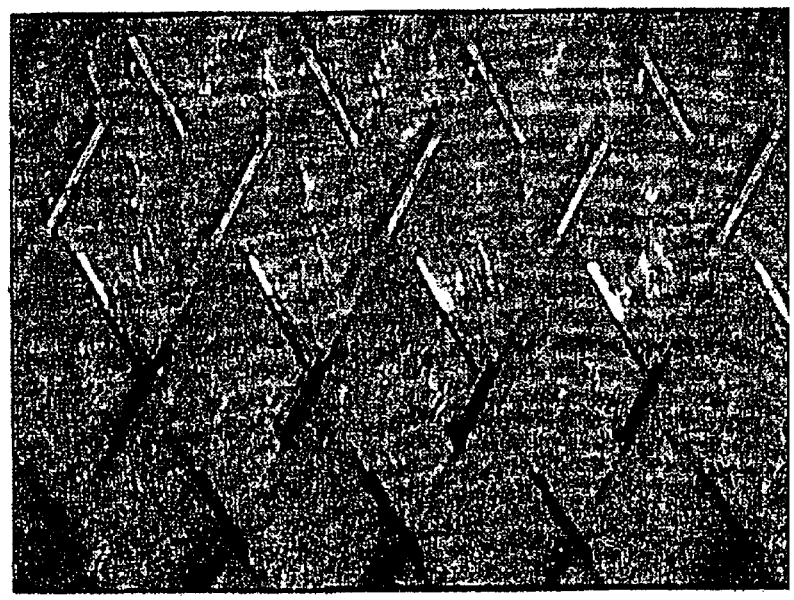
Figure 12:
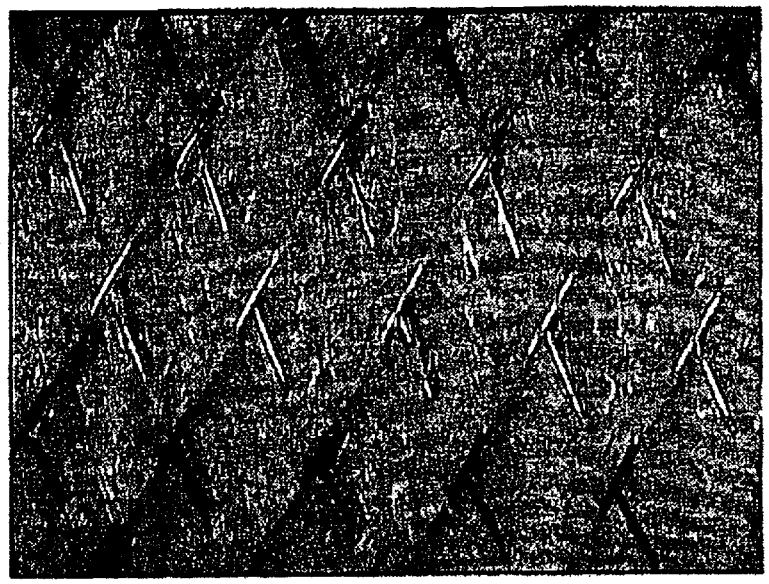
Figure 13:
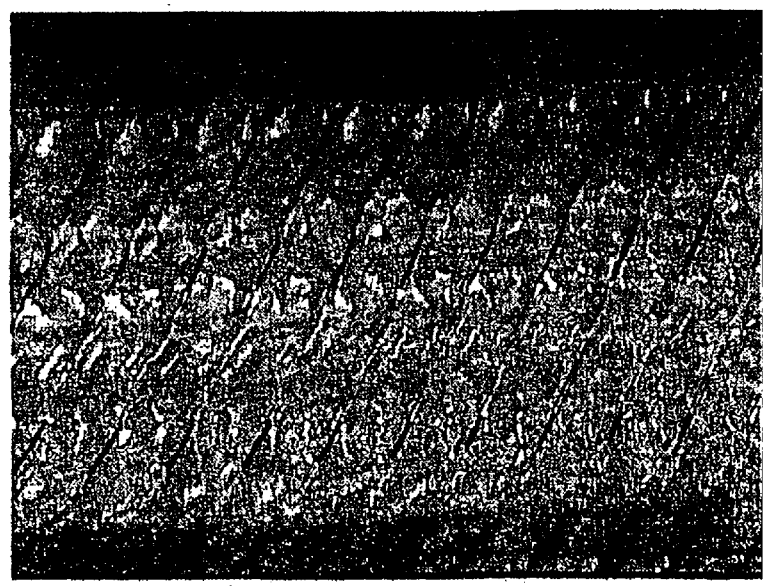
Figure 14:
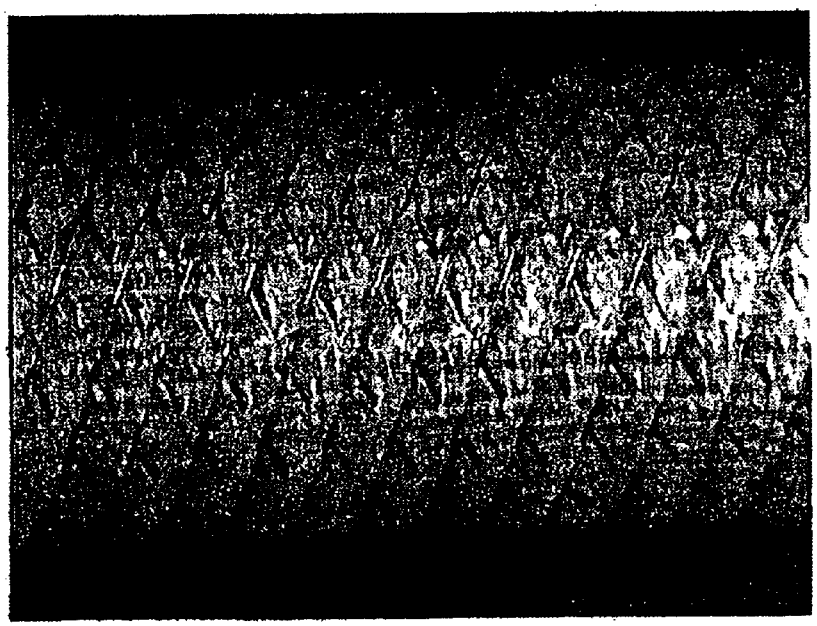
Figure 15:
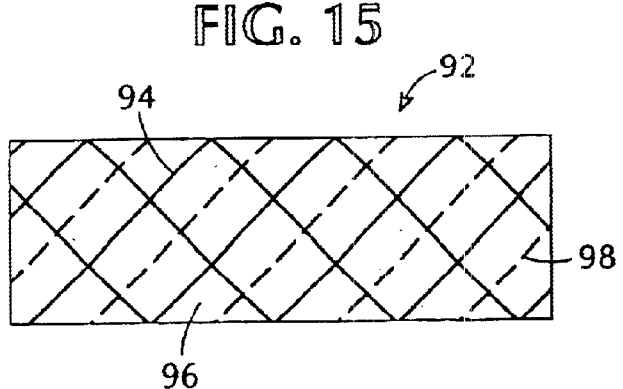
Figure 16:
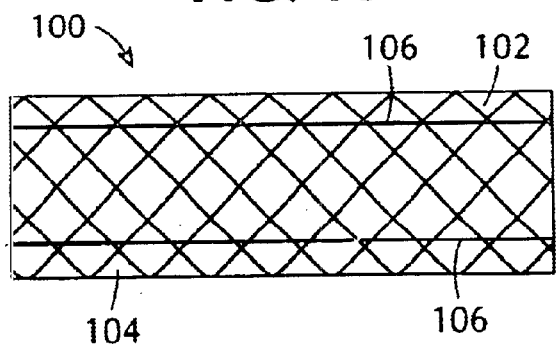
Figure 17:
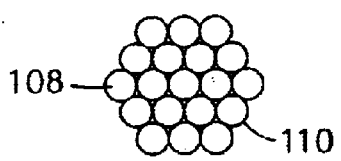
Figure 18:
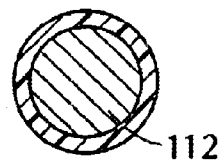
Figure 19:
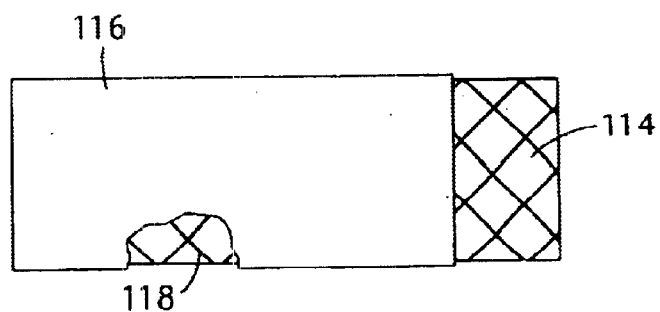

FIGS. 7 and 8 schematically illustrate a process for manufacturing the prosthesis;

FIGS. 9 and 10 schematically illustrate an alternative process for manufacturing the prosthesis;

FIGS. 11a and 11b are photographs of a prosthesis constructed according to a first exemplary process according to the present invention;

FIG. 12 is a photograph of a prosthesis constructed according to a second exemplary process;

FIG. 13 is a photograph of a prosthesis constructed according to a third exemplary process;

FIG. 14 is a photograph of a prosthesis constructed according to a fourth exemplary process;

FIG. 15 is a diagrammatic view of an alternative embodiment prosthesis;

FIG. 16 is an illustration of another alternative embodiment prosthesis;

FIG. 17 illustrates a coated multifilament yarn of a further alternative embodiment prosthesis;

FIG. 18 illustrates a coated structural strand of another alternative embodiment prosthesis; and FIG. 19 illustrates a further alternative embodiment coated prosthesis.

DETAILED DESCRIPTION OF THE PREFERRED EMBODIMENTS

Turning now to the drawings, there is shown in FIG. 1 a deployment device 16 for delivering a prosthesis 18 to an intended fixation location or treatment site within a body lumen, and then controllably releasing the prosthesis for radial self-expansion and fixation within the lumen.

The device includes an elongate and flexible outer catheter 20 constructed of a biocompatible polymer, e.g. polyurethane. A central lumen 22 runs the length of catheter 20. A distal portion 24 of the outer catheter surrounds prosthesis 18. An inner catheter 26 is contained within lumen 22 and runs along substantially the entire length of outer catheter 20. At the distal end of inner catheter 26 is a tapered distal tip 28. Prosthesis 18 surrounds inner catheter 26, and thus is confined between the inner and outer catheters. A lumen 30 in the inner catheter can accommodate a flexible guidewire.

Prosthesis 18, shown completely rather than in section, is a tubular braided structure including helically wound monofilament structural strands 32 formed of a resilient material. In FIG. 1, prosthesis 18 is elastically compressed into a reduced radius axially elongated delivery state. Outer catheter 20 confines the prosthesis, maintaining it in the delivery state against an elastic restoring force.

An annular detent 34, mounted to inner catheter 26, occupies a space between the inner and outer catheters to limit proximal travel of prosthesis 18 relative to the inner catheter. Thus, as outer catheter 20 is moved proximally relative to inner catheter 26, the detent prevents the prosthesis from moving with the outer catheter.

Catheters 20 and 26, while maintaining prosthesis 18 in the delivery configuration, are moved translumenally, e.g. through vasculature, to deliver the prosthesis to the intended treatment site once the prosthesis is positioned as intended, inner catheter 26 is held stationary, while outer catheter 20 is withdrawn proximally. Detent 34 prevents prosthesis 18 from moving proximally with the outer catheter, thus to maintain the prosthesis properly aligned as it progressively radially self-expands toward a relaxed state and into intimate contact with tissue at the treatment site. Because the prosthesis does not expand completely to the relaxed state, it exerts a residual force on the tissue that tends to maintain fixation of the prosthesis. At this point the prosthesis has a diameter much larger than the diameter of distal tip 28, so that the inner catheter and tip, along with the outer catheter, are easily proximally withdrawn.

Prosthesis 18 resembles a radially self-expanding stent, in that it is well suited for radially compressed delivery and self-expansion. Accordingly, familiarity with radially self-expanding stents is useful in considering prosthesis 18.

Figure 2A:
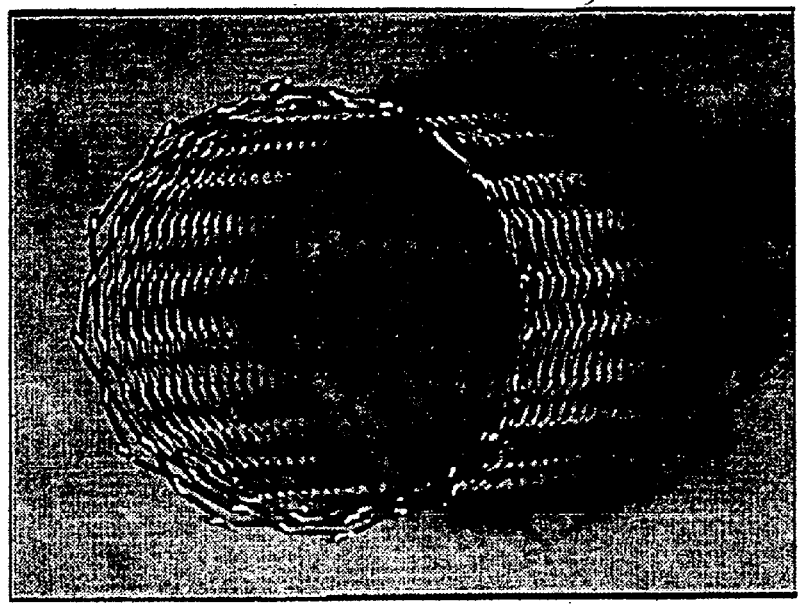
FIGS. 2a and 2b illustrate an open weave stent consisting of resilient metal structural strands.
Figure 2B:
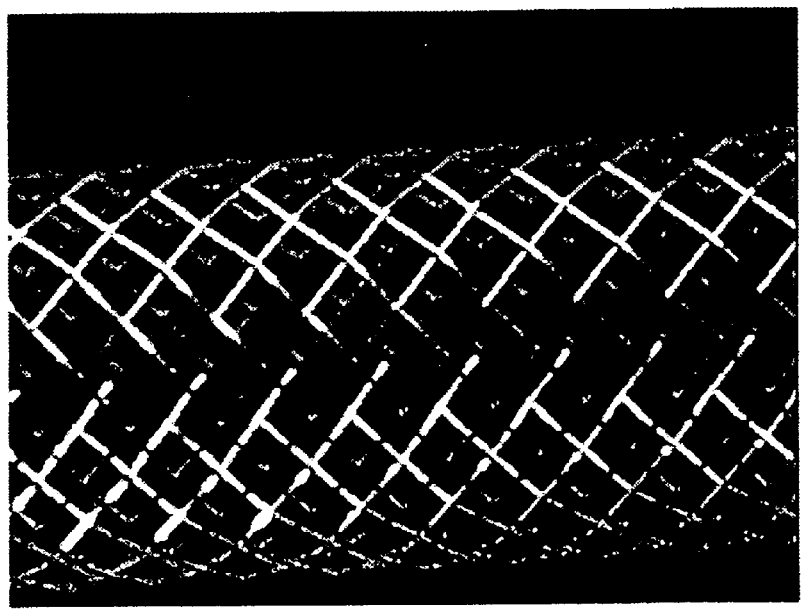

A radially self-expanding stent is pictured in FIGS. 2a and 2b. The stent consists of two oppositely directed and concentric sets of helically wound thread elements or wires. The wires can be formed of metal or a polymeric material and have good elastic recovery. Each wire is selectively shaped so that its nominal shape, i.e. its shape when in a relaxed state subject to no external stresses, is helical. The wires cooperate to give the stent its nominal tubular shape.

Adjacent helices in two opposite winding directions are spaced apart axially, resulting in rhombotic voids or interstices with dimensions substantially larger than the wire diameters. The open-mesh construction, in combination with the resiliency and strength of the selectively shaped wires, enables and facilitates (a) elastic compression of the stent to a much smaller radius suitable for intraluminal delivery; (b) virtually instantaneous radial expansion of the stent when released at a treatment site; and (c) a sufficient residual force to ensure acute fixation without hooks or barbs, although such fixation options may enhance fixation.

With reference to FIGS. 3 and 4 it can be appreciated that structural strands 32 form a latticework 35 of prosthesis 18. Like the wires of the stent, strands 32 are arranged in two oppositely directed and concentric sets of helices, spaced apart axially from one another to define rhombotic interstices. Structural strands 32 further are similar to the wires in that they exhibit the requisite strength and elasticity, are biocompatible, resistant to fatigue and corrosion, and in vascular applications are hemocompatible as well. Materials meeting these needs include certain stainless "spring" steels, cobalt-based alloys, and alloys containing titanium. Several preferred cobalt-based alloys are sold under the brand names "Elgiloy", "Phynox" and "MP35N".

Particularly preferred CoCrMO alloys are described in U.S. patent application Ser. No. 08/640,253 (now U.S. Pat. No. 5,891,191) entitled "Cobalt-Chromium-Molybdenum Alloy Stent and Stent Graft" (J. Stinson), assigned to the assignee of this application and filed concurrently herewith. These alloys contain less than about 5 weight percent nickel, preferably less than about 2 weight percent nickel and more preferably no more than about 1 weight percent nickel. Chromium is preferably present in an amount between about 26.0 and 30.0 weight percent, and molybdenum preferably in an amount between about 5.0 and 7.0 weight percent. The alloys further can include nitrogen in an amount up to about 0.25 weight percent, and carbon in an amount up to about 0.35 weight percent. Other elements, preferably in amounts no greater than about 1.0 weight percent, include iron, silicon, manganese, copper, phosphorous, sulfur and tungsten. The balance of the alloy in each case can be cobalt, preferably in an amount of at least 60.0 weight percent. Specific examples are described in this application, which is incorporated by reference herein.

A preferred alloy of titanium is a recovery metal alloy of nickel and titanium, sold under the brand name "Nitinol". Other titanium alloys are disclosed in U.S. patent application Ser. No. 08/598,751 entitled "Titanium Alloy Self-Expanding Stent", filed Feb. 8, 1996 and assigned to the assignee of this application. Other suitable titanium alloys include titanium-zirconium-niobium alloys and a titanium-aluminum-vanadium alloy known as TI-6Al-4V.

Suitable polymeric monofilaments include PET, polypropylene, PEEK, HDPE, polysulfone, acetyl, PTFE, FEP, polycarbonate urethane and polyurethane. Suitable polyurethanes and polycarbonate urethanes include those sold under the following brand names: Chronoflex AR, Chronoflex Al, Corethane, and Biomer. These monofilaments preferably have diameters in the range of about 0.002–0.015 inches (0.051–0.38 mm).

As seen in FIG. 4, structural strands 32 intersect each other to define a braid angle α, which is bisected by a longitudinal axis 36 of the prosthesis. The braid angle, when prosthesis 18 is in the relaxed state, is in the range of about 60 to 150 degrees, and more preferably 80 to 140 degrees.

As seen in FIG. 3, radial compression of the prosthesis substantially reduces the braid angle. The braid angle largely determines the relationship between radial compression and axial elongation of the prosthesis. More particularly, smaller braid angles yield less axial shortening for a given amount of radial expansion. On the other hand, for a given strand size and strength, a larger braid angle imparts greater resistance to radial compression and more positive acute fixation. Accordingly a smaller braid angle generally requires a structural strand that is resilient, but stronger, i.e. with a higher modulus of elasticity.

Figure 5:
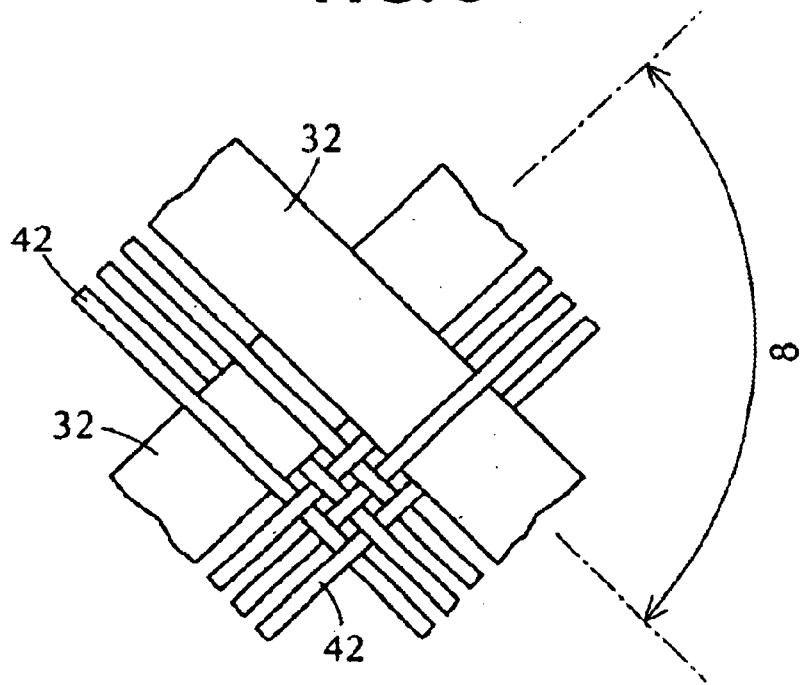
FIG. 5 is an enlarged partial view of FIG. 3, schematically illustrating an interbraiding of structural and textile strands of the prosthesis.

The interstices 38 between adjacent structural strands in prosthesis 18 are occupied by a textile sheeting or fabric 40. As seen in FIG. 5, sheeting 40 is formed of multiple textile strands 42 interbraided with one another and further interbraided with structural strands 32. Strands 32 and 42 are illustrated in a one over one braiding pattern. However, it is to be appreciated that a variety of braiding patterns are known to those skilled in the art, and the pattern most suitable in a given instance depends on desired structural characteristics and materials involved. Textile strands 42 also are provided in sets of oppositely directed helices, and intersect one another at the same braid angle a defined by the structural strands. Textile strands 42 preferably are multifilament yarns, although they can be monofilaments. In either event the textile strands are much finer than the structural strands, ranging from about 10 to 400 denier. Individual filaments of the multifilament yarns can range from about 0.25 to about 10 denier. The multifilament yarns generally have a high degree of compliance, which may or may not include elasticity. Suitable materials include PET, polypropylene, polyurethane, polycarbonate urethane, HDPE, polyethene, silicone, PTFE, ePTFE and polyolefin. One suitable high molecular weight polyethylene is sold under the brand name "Spectra".

Due to the fineness of textile strands 42 and a close or tight weave, textile sheeting 40 can be microporous, yet essentially impervious to body fluids. Also, the textile sheeting is highly compliant, conforming to changes in the shape of latticework 35 as prosthesis 18 either radially self-expands or is radially compressed. The shape of latticework 35 determines the shape of the prosthesis.

Figure 6:
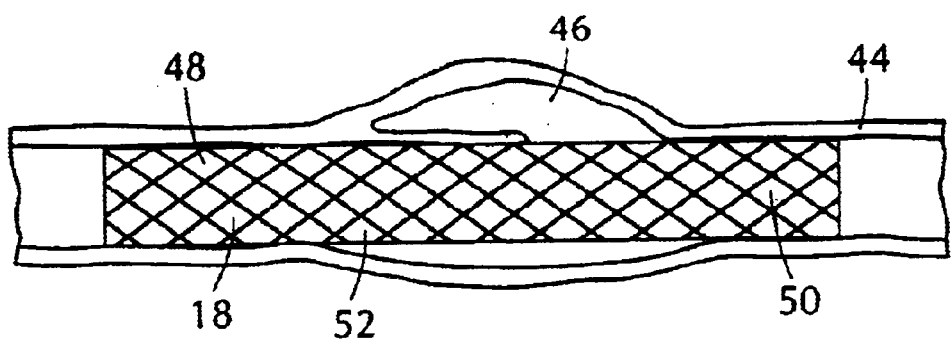
FIG. 6 shows the prosthesis of FIG. 1 deployed within a vessel and spanning an aneurysm.

Thus, prosthesis 18 combines the favorable attributes of self-expanding stents and grafts. Latticework 35 provides radial compressibility, self-expansion over a wide range of radii and residual force for acute fixation, while textile sheeting 40 reduces permeability to the extent that the prosthesis is essentially impervious to blood and other body fluids. For these reasons, prosthesis 18 is particularly well suited to treating an aneurysm. FIG. 6 illustrates fixation of prosthesis 18 within a blood vessel having a vessel wall 44. Along the vessel wall is in an aneurysm 46. Opposite end regions 48 and 50 of the prosthesis have radially expanded into intimate contact with vessel wall 44 on opposite sides of the aneurysm. A medial region 52 of the prosthesis spans the aneurysm. End regions 48 and 50 effectively fix the prosthesis, due to the resilience and strength of the structural strand latticework. At the same time the prosthesis, because of textile sheeting 40, shunts blood past the aneurysm preventing any substantial leakage into the aneurysmal sack.

A particularly favorable structure for prosthesis 18 is an interbraiding of metallic structural strands with Dacron (polyester) multifilament yarns as the textile strands. The metal structural strands exhibit high strength in terms of elastic moduli. For example, stainless steels can have elastic moduli of about $28-30 \times 10^6$ psi. Titanium and alloys of titanium tend to have elastic moduli in the range of $15.4-16.6 \times 10^6$ psi. In contrast polyethylene, for example, has an elastic modulus in the range of about $0.02-0.055 \times 10^6$ psi, and other polymeric materials have elastic moduli in this order of magnitude. Accordingly, for a given strand diameter, helical diameter and helical pitch, a latticework of metallic strands is considerably more resistant to radial compression, and provides a greater residual force for acute fixation. The Dacron polyester multifilament yarn has a high elastic recovery and elongation (up to 36% for the polyester fiber) and a low elastic modulus, which ensure that textile sheeting 40 conforms to the latticework.

This favorable composite structure cannot be manufactured by forming a braided structure on a mandrel, then heating the mandrel to thermally set the strands in their helical shapes. Thermally setting metallic structural strands entails heating the strands to temperatures up to about 1000° C. while the strands are maintained in the intended helical shape. Such temperatures are well above the melting points of polyesters and other materials most suitable for the multifilament yarn textile strands. Selectively shaping the structural strands is important in enhancing the predictability and control over prosthesis contractions and expansions, and also reduces any tendency of the prosthesis to unravel.

To attain favorable characteristics of stents and grafts, prosthesis 18 can be fabricated according to several steps as illustrated in FIGS. 7 and 8. FIG. 7 shows two structural strands (metal monofilaments) 32a and 32b, one from each set of oppositely directed structural strands, wound about a mandrel 54 and supported by respective bobbins 56 and 58. While just strands 32a and 32b are illustrated as a matter of convenience, it is to be appreciated that all of the structural strands are wound about the mandrel and maintained together for shaping. Only structural strands are present, however, as shaping occurs before interbraiding with the textile strands.

Age-hardening is accomplished within a furnace 60 in a vacuum or a protective atmosphere. Temperatures are within the range of about 350–1000° C., with the specific temperature depending on the structural material. The filaments overlie one another to form multiple intersections, one of which is indicated at 62. Bobbins, including 56 and 58, are set to tension their respective strands during age-hardening. The appropriate duration for age-hardening varies with materials and dimensions, but can range from as brief as 30 seconds, to about 5 hours.

After age-hardening, the structural strands are allowed to cool, whereupon each structural strand retains the helical shape as its nominal shape. In the context of elastic materials, "nominal shape" refers to the shape in a relaxed state, i.e. when under no external stress. The age-hardened metallic monofilaments are highly resilient, i.e. deformable under external stress but elastically returning to the nominal shape when free of the external stress. The strands when constructed of a recovery metal are plastically deformable when maintained below an activation temperature, which for Nitinol can be below body temperature (about 37° C.). When heated to the activation temperature or above, the structural strand returns to the selected nominal shape. In this context the "nominal shape" is the shape to which the strand returns when at or above the activation temperature.

When structural strands 32 are thermoplastic rather than metallic monofilaments, multiple strands are thermally set in similar fashion. More particularly, with the thermoplastic monofilaments wound in opposite sets about mandrel 54, the strands are heated to a heat-forming temperature in the range of about 100 to 400° C., more preferably 150 to 250° C., either within a furnace as previously described or by heating the mandrel. The strands are maintained at or above the heat-forming temperature for a duration generally shorter than that of thermally setting metal strands, i.e. from about 30 seconds to about 2 hours, or more preferably 5 to 15 minutes. Again, only the structural strands are shaped, and before they are interbraided with the textile strands. This sequence can be advantageous even when the structural strands and textile strands are formed of the same thermoplastic material, as it enables fabrication of a prosthesis in which only the structural strands are thermally set.

It is to be appreciated that the thermal setting process alters the structural strands, in the sense of changing their shapes from an original or first nominal shape to a second, selected nominal shape. Typically the original nominal shape is linear, with the selected nominal shape determined by the diameter of the mandrel and the pitch at which the structural strands are wound about the mandrel.

Interbraiding of the structural and textile strands occurs after selective shaping. FIG. 8 schematically illustrates a braiding apparatus 64 including an annular carrier assembly 66 including a circular array of bobbins, two of which are indicated at 68 and 70. The apparatus further includes a mandrel 72, centered within the annular assembly and movable longitudinally relative to the assembly as indicated by the arrow.

While those skilled in the art are acquainted with the use of braiding machinery, braiding apparatus 64 is used as follows:

First, carrier assembly 66 is loaded by winding different strands onto different bobbins. The type of strand wound on each bobbin depends on the desired braiding pattern and ratio of structural strands to textile strands. All strands are drawn from their respective bobbins to mandrel 72, and braiding proceeds by moving mandrel 72 longitudinally, while at the same time the bobbins are moved relative to one another as dictated by the desired pattern of braiding, e.g. a two-dimensional maypole braiding. The result is a simultaneous interbraiding of the structural and textile strands onto the mandrel, as indicated at 74. The mandrel determines the diameter of the braided structure. Mandrel longitudinal speed largely determines the braid angle. Prosthesis lengths are determined by the duration of braiding, or by cutting the braided structure to predetermined lengths upon its removal from the mandrel.

The braiding process includes controlling the structural strands as to orientation during braiding, to ensure that the individual helices cooperate to provide the desired nominal tubular configuration for the resulting latticework. Similar control of the textile strands is not necessary, due to their more compliant nature. Properly oriented structural strands diminish any unraveling tendency and result in more predictable contraction and expansion of the prosthesis. Further, from FIG. 5 it can be appreciated that the textile strands, in filling the interstices between structural strands, tend to maintain the structural strands in the desired configuration of intersecting helices.

FIG. 9 schematically illustrates an alternative braiding apparatus 76 in which the structural strands are selectively shaped by cold-working. In particular, an annular carrier assembly 78 is mounted concentrically on a longitudinally movable mandrel 80. As before, the carrier assembly supports multiple bobbins in a circular array, with two of the bobbins being shown at 82 and 84. A structural strand 32 has been wound on the bobbin 82, while bobbin 84 carries a textile strand 42. The structural strand is not thermally shaped before braiding, and thus at first has a linear nominal shape.

Structural strand 32 is plastically deformed by cold working as it travels from bobbin 82 to the mandrel. A small diameter shaping pulley 86 and a larger diameter idler pulley 88 are disposed along the path traversed by strand 32. Shaping pulley 86 exerts a bending stress on the moving structural strand trained about this pulley, particularly on radially outward portions of the strand. Although both pulleys are shown in side elevation, it is to be understood that shaping pulley 88 actually is orthogonal to idler pulley 88 to impart the selected nominal shape. Bobbin 82 is supported on a carrier that includes a clutch (not shown) adjustable to control the tension applied to the strand, thereby to adjust the amount of bending stress.

The tension is controlled so that the bending stress, at least along the radially outward portions of the strand along pulley 86, exceeds the yield stress of the material. The appropriate level of tension is within the range of about 200–1000 gms, depending on such factors as the material, the monofilament diameter, and the bending radius about pulley 86. The result is a cold-working plastic deformation, represented as a hatched segment 90 in FIG. 10. It is to be appreciated that segment 90 is greatly exaggerated and intended for illustration only. The actual plastic flow is less pronounced and continuous, and changes the nominal shape of the structural strand from linear to helical. Further in this connection, it is noted that pulley 86 would impart a curved nominal shape to the structural strand in any event, and that the helical nominal shape with the desired pitch is obtained through proper orientation of the pulley with respect to the carrier assembly while the desired tension in the strand is maintained.

The CoCrMO alloys described in the aforementioned U.S. patent application Ser. No. 08/640,253 (now U.S. Pat. No. 5,891,191) entitled "Cobalt-Chromium-Molybdenum Alloy Stent and Stent Graft" are particularly well suited for this approach. the selective shaping and braiding steps can occur closely in time and within a continuous process. In contrast, thermal shaping is followed by cooling the strands and winding the strands onto bobbins, and therefore involves processing in a batch mode.

FIGS. 11–14 are photographs of four different braiding structures, formed according to the following examples of the braiding process. In Examples 1–3, the metallic monofilaments are thermally shaped prior to braiding, although they can just as well be plastically formed to achieve the same result.

EXAMPLE 1

The bobbins of a braider carrier assembly are loaded with seventy-two textile filaments, each being a 100 denier polyester yarn composed of seventy filaments. At every third carrier around the braider, a structural strand is wound for co-braiding with the multifilament yarn, to provide twelve structural strands in each of two opposite winding directions. Each structural strand is an Elgiloy wire having a diameter of 0.0043 inches (0.11 mm). The strands are braided in a two over two braiding pattern onto an 8 mm diameter round mandrel, with the braider operated to determine a braid angle of 110°. The braid is formed to an adequate length, then removed from the mandrel.

The resulting interbraided structure, shown in FIGS. 11a and 11b, is a tubular composite of the polyester yarn and metal monofilaments. The wire latticework is formed as two sets of oppositely directed helices, with the wires in a two over two braided pattern.

EXAMPLE 2

Again, carrier bobbins are loaded with seventy-two polyester yarns of 100 denier and seventy filaments. A 0.0043 inch diameter Elgiloy wire, provided at every fourth carrier, is co-braided with the multifilament yarn to provide nine wires in each of two opposite winding directions. The strands are braided in a two over two braiding pattern on an 8 mm diameter round mandrel. The result, pictured in FIG. 12, is a tubular interbraided structure of polyester yarn and metal monofilaments. The wire substructure consists of two concentric sets of oppositely directed helices, not interbraided but overlying one another.

EXAMPLE 3

The carrier bobbins are loaded with seventy-two 100 denier polyester yarns formed of seventy filaments. A 0.0043 inch diameter Elgiloy wire is loaded at every other carrier around the braider in only one of two opposite winding directions, for a total of eighteen wires co-braided with the multifilament yarn. The strands are braided on an 8 mm diameter round mandrel in a two over two braiding pattern, with the braider set to form a braid angle of 110°. The result (FIG. 13) is a hollow tubular interbraided structure of polyester yarn and metal monofilaments. The wire substructure consists of a single layer of eighteen axially spaced helices in one winding direction.

EXAMPLE 4

Carrier bobbins are loaded with one hundred forty-four polyester yarns of 100 denier and seventy filaments. An Elgiloy wire of 0.0055 inches (0.13 mm) is loaded at every sixth carrier around the braider, to provide twelve wires in each of two opposite winding directions for co-braiding with the multifilament yarn. Prior to loading, the Elgiloy wire is plastically formed into the desired shape as described in connection with FIGS. 9 and 10. The strands are braided onto a 16 mm diameter round mandrel, with the braider set to provide a braid angle of 110°. The result, shown in FIG. 14, is a tubular interbraided structure of polyester yarn and metal monofilaments, including a wire substructure consisting of twenty-four wires braided in a one over one braiding pattern.

EXAMPLE 5

The carrier bobbins are loaded with ninety-six polyester yarns of 100 denier and seventy filaments. A 0.0055 inch diameter Elgiloy wire is loaded at every third carrier around the braider, to provide sixteen wires in each of two opposite winding directions for co-braiding with the multifilament yarn. The strands are braided in a two over two braiding pattern on a 12 mm diameter round mandrel, with the braider set to provide a braid angle of 110°. The result is a tubular interbraided structure of the polyester yarn and metal monofilaments, including a wire substructure of thirty-two wires braided in a two over two pattern.

In all of these examples, the resulting prosthesis has water permeability comparable to that of a vascular graft, and can be constrained to a reduced diameter and allowed to expand like a radially self-expanding stent.

The prosthesis fabricating processes can be enhanced to impart a variety of desired characteristics to the resulting prosthesis. For example, FIG. 15 shows a prosthesis 92 formed of helical structural strands 94 interbraided with multifilament yarns forming a textile sheeting 96. A further strand 98 is interbraided with the textile strands. Strand 98 is formed of a radiopaque material, e.g. tantalum. Strand 98 improves the fluoroscopic imaging of prosthesis 92 at or near a treatment site, to facilitate recognition of proper placement or a need to move the prosthesis. Other approaches to enhancing radiopacity include use of composite structural strands (e.g. wires with radiopaque cores), plated monofilaments, radiopaque inks and marker bands.

FIG. 16 illustrates a prosthesis 100 fabricated according to the following example:

EXAMPLE 6

A braiding device is provided with eighteen triaxial guide tubes arranged about the carrier assembly. The bobbins are loaded with seventy-two polyester yarns of 100 denier and seventy filaments. Every third carrier around the braider is loaded with a 0.0043 diameter Elgiloy wire, to provide twelve wires in each of two opposite winding directions for co-braiding with the multifilament yarns. Eighteen aliphatic polyurethane monofilaments of 0.004 inches (0.1 mm) in diameter are provided, one such monofilament fed into each of the triaxial guide tubes for incorporation into the braided structure as axial runners. The strands are braided about an 8 mm diameter round mandrel in a two over two braiding pattern, with the braiding device set to provide a braid angle of 110°. Following braiding, the prosthesis is removed and heated in an oven at 150° C. for approximately ten minutes to melt the polyurethane runners, thereby fusing them to the remaining structure.

The result is tubular interbraided prosthesis 100, incorporating metal monofilaments 102, a sheeting 104 of the polyester yarns, and axial polyurethane runners 106. The wire substructure is braided in a two over two braiding pattern. The prosthesis has a water permeability comparable to that of a vascular graft, and can be constrained radially and allowed to self-expand like a self-expanding stent. Radial recovery is enhanced and the tendency to unravel or fray when cut is reduced, due to the axial runners.

Another approach to reduce unraveling of the prosthesis is to apply a silicone adhesive to the opposite ends, or to submerge the prosthesis ends into a solution of a polyurethane, a silicone, or a polycarbonate urethane and a solvent having a low percentage of solids. Residual polyurethane, silicone or polycarbonate urethane remains after drying and tends to prevent unraveling.

FIG. 17 illustrates a multifilament yarn 108 with a coating 110 of TFE, or alternatively a copolymer of TFE and silicone. Coating 110 is applied by plasma polymerization prior to braiding. Coating 110 enhances surface properties of the yarn, for example by reducing friction. A prosthesis incorporating a sheeting composed of the coated yarns 108 can be deployed with less force. Also, inflammatory responses to the implanted stent may be reduced. An alternative approach, namely plasma polymerization of the stent after braiding, achieves substantially the same result.

According to another process enhancement, structural strands 112 in FIG. 18, particularly metal monofilaments, are coated with PTFE, ePTFE, polypropylene, polyethylene, PET, or polyurethane. Coating may occur after selective shaping and before braiding, by over-extrusion, tape wrapping, serving or by an additional braiding step. This reduces exposure of the blood flow to metal.

The process also can be augmented with a surface coating step after braiding, to provide a prosthesis 114 with a surface coating 116 as illustrated in FIG. 19. A portion of the coating is removed to illustrate a covered portion of the prosthesis. At least one end of prosthesis 114 can be left uncovered as indicated at 118, to enhance acute fixation at the exposed end. Alternatively, the prosthesis can be coated over its entire length. A surface coating of heparin or coumadin reduces thrombogenicity. A surface coating of steroids, e.g.

dexamethasone, reduces the restenosis rate. Finally, coatings of albumin, collagen or gelatin can be incorporated to provide an acute reduction in permeability of the textile sheeting.

Further modifications to enhance-utility for specific applications, include using a tapered mandrel for heat setting the structural strands, to form a tapered prosthesis. To reduce migration, prosthesis can be provided with flared ends, or may be braided with end portions that do not incorporate the multifilament yarns. Collagen, PGA and other biological or bioabsorbable materials can be substituted for portions of the monofilament or multifilament strands. Metallocene catalized polymers, e.g. polyolefins or polypropylene, and fluorination if desired, may also be incorporated.

Yet another modified approach utilizes three-dimensional braiding, as described in U.S. application Ser. No. 08/640,091 (now U.S. Pat. No. 5,718,159) entitled "Three-Dimensional Braided Covered Stent" (P. Thompson), assigned to the assignee of this application and filed concurrently herewith.

Thus, in accordance with the present invention, a prosthesis incorporates structural strands interbraided with more tightly woven textile strands that reduce permeability. The structural strands are selectively shaped before their interbraiding with the textile strands, either by a thermal set or by selective plastic deformation, and in either event are shaped without adversely affecting the textile strands. Plastic deformation of structural strands by cold-working is advantageous in permitting a continuous process of cold-working followed by interbraiding. The result is an interbraided prosthesis incorporating the strength, resilience and range of radii associated with self-expanding stents, and the impermeability associated with vascular grafts, in which a selective shaping of the structural strands does not limit the range of materials useable as additional strands in the interbraided structure to reduce permeability, alter porosity, reduce friction or enhance fluoroscopic imaging.

The scope of this disclosure is intended to comprehend the subject matter of the patent applications and publications identified herein. Accordingly, these applications and publications are incorporated by reference.

What is claimed is:

1. A medical device including:

an elongate and flexible catheter;

a braided prosthesis mounted to the catheter at a distal end thereof in surrounding relation thereto, said prosthesis including an interbraiding of a plurality of structural strands and a plurality of textile strands being more compliant than the structural strands and having a textile strand melting temperature;

wherein the structural strands are formed of a structural material and have respective nominal strand shapes when in a relaxed state under no external stress, and further are elastically deformable away from their respective nominal strand shapes, wherein each of the structural strands is adapted to be altered to acquire a selected nominal strand shape different from an original nominal strand shape according to a shape-altering step selected from the group consisting of:

(1) a selective plastic deformation including application of a bending stress sufficient to cause a plastic flow and thereby alter the nominal strand shape from the original nominal strand shape to the selected nominal strand shape, wherein the structural strands are resilient and ductile; and (2) a selective thermal setting including a heating of the structural strands at least to a heat set temperature while maintaining the structural strands in their respective selected nominal strand shapes, wherein the structural strands are susceptible to said selective thermal setting only when heated at least to the heat set temperature;

wherein the structural strands are so altered, and when in the respective selected nominal strand shapes form windings having tubular profiles, and further have selected orientations within the prosthesis to impart to the prosthesis a tubular predetermined nominal shape corresponding to said tubular profiles; and wherein the heat set temperature is higher than the textile strand melting temperature.

2. The device of claim 1 further including:

a means for releasably maintaining the prosthesis at the distal end of the catheter in a resiliently radially compressed state, and operable to release the prosthesis for a radial self-expansion at an intraluminal treatment site.

3. A prosthesis, including:

an integrated structure including an interbraiding of a plurality of resilient structural strands formed of a structural material and a plurality of textile strands being more compliant than the structural strands and having a textile strand melting temperature;

wherein each of the structural strands has a nominal shape when in a relaxed state under no external stress, and further is thermally formable to a acquire a selected nominal strand shape different from an original nominal strand shape in response to a heating of the structural strand at least to a thermal forming temperature while maintaining the structural strand in the selected nominal strand shape, and wherein said structural strands are thermally formable only when heated at least to the thermal forming temperature;

characterized in that the structural strands are thermally formed into their respective selected nominal strand shapes, form windings having tubular profiles in their selected nominal strand shapes, and are selectively oriented within the integrated structure to impart to the integrated structure a tubular predetermined nominal configuration corresponding to said tubular profiles;

further characterized in that said melting temperature of the compliant textile strands is lower than said thermal forming temperature.

4. The prosthesis of claim 3 wherein:

the structural strands cooperate to form a latticework, and the textile strands cooperate to form a textile sheeting supported by the latticework and occupying interstices between adjacent structural strands of the latticework.

5. The prosthesis of claim 3 wherein:

said structural strands are monofilaments.

6. The prosthesis of claim 5 wherein:

said monofilaments are metal, and formed of at least one of the materials selected from the group consisting of: stainless steel, an alloy including cobalt, and an alloy including titanium.

7. The prosthesis of claim 5 wherein:

said monofilaments are polymeric, and constructed of at least one of the materials selected from the group consisting of:

PET (polyethyleneterepthalate), polypropylene, PEEK (polyetherketone), HDPE (high density polyethylene), polysulfone, PTFE (polytetrafluoroethylene), FEP (fluorinated ethylene propylene), polycarbonate urethane, and polyurethane.

8. The prosthesis of claim 5 wherein:

said monofilaments have diameters in the range of about 0.002–0.015 inches.

9. The prosthesis of claim 3 wherein:

said textile strands are multifilament yarns in the range of about 10–400 denier.

10. The prosthesis of claim 9 wherein:

said multifilament yarns are composed of filaments in the range of about 0.25–10 denier.

11. The prosthesis of claim 9 wherein:

said multifilament yarns are formed of at least one of the materials selected from the group consisting of: PET (polyethyleneterepthalate), polypropylene, polyurethane, polycarbonate urethane, HDPE (high density polyethylene), polyethylene, silicone, -PTFE (polytetrafluoroethylene), ePTFE (expanded polytetrafluoroethylene), and polyolefin.

12. The prosthesis of claim 3 wherein:

said selected nominal strand shapes of the structural strands are helical.

13. The prosthesis of claim 12 wherein:

said structural strands cooperate to form a latticework including first and second sets of helices running in respective first and second opposite directions, whereby the interstices of the latticework are rhombic.

14. The prosthesis of claim 13 wherein:

the first and second sets of helices define a braid angle in the range of about 60–150 degrees.

15. The prosthesis of claim 3 wherein:

said integrated structure consists essentially of a single layer of the interbraided structural strands and textile strands.

16. The device of claim 1 wherein:

the selected nominal strand shapes are helical.

17. The device of claim 16 wherein:

the structural strands cooperate to form a latticework including first and second sets of helices running in respective first and second opposite directions.

18. The device of claim 1 wherein:

said structural strands are formed of a metal selected from the group consisting of: stainless steel, an alloy including cobalt, and an alloy including titanium.

19. The device of claim 18 wherein:

the structural strands are formed of a cobalt-chromium-molybdenum alloy.

20. The device of claim 1 wherein:

the structural strands are monofilaments formed of a polymeric material selected from the group consisting of: PET, polypropylene, PEEK, HDPE, polysulfone, PTFE, FEP, polycarbonate urethane, and polyurethane.

21. The device of claim 1 wherein:

said textile strands are multifilament yarns formed of a material selected from the group consisting of: PET, polypropylene, polyurethane, polycarbonate urethane, HDPE, polyethylene, silicone, PTFE, ePTFE, and polyolefin.

22. The device of claim 1 wherein:

said interbraiding of the structural strands and the compliant textile strands consists essentially of a single layer.

* * * * *